United States Patent [19]
Knifton

[11] 4,315,993
[45] Feb. 16, 1982

[54] PREPARATION OF ETHYLENE GLYCOL
[75] Inventor: John F. Knifton, Austin, Tex.
[73] Assignee: Texaco Inc., White Plains, N.Y.
[21] Appl. No.: 219,073
[22] Filed: Dec. 22, 1980
[51] Int. Cl.$^3$ ............................................. C07C 27/06
[52] U.S. Cl. .............................. 518/700; 252/431 R; 252/431 N; 252/431 P
[58] Field of Search ........................................ 518/700
[56] References Cited
U.S. PATENT DOCUMENTS
2,549,470 4/1951 Howk et al. ....................... 518/700

Primary Examiner—Howard T. Mars
Attorney, Agent, or Firm—Carl G. Ries; Jack H. Park; Walter D. Hunter

[57] ABSTRACT

A process for preparing ethylene glycol wherein a mixture of carbon monoxide and hydrogen is contacted at an elevated temperature and pressure and in the presence of a solvent with a ruthenium compound and a promoter, such as pyrocatechol. In another aspect this invention relates to the preparation of ethylene glycol ethers from carbon monoxide and hydrogen.

15 Claims, No Drawings

PREPARATION OF ETHYLENE GLYCOL

BACKGROUND OF THE INVENTION

1. Field of the Invention

This invention relates to a process for preparing ethylene glycol by reaction of carbon monoxide and hydrogen in the presence of a catalyst, a promoter and a solvent. In another embodiment, this invention is concerned with the preparation of ethylene glycol ethers from carbon monoxide and hydrogen.

2. Prior Art

In recent years, a large number of patents have been issued dealing with the synthesis of lower molecular weight hydrocarbons, olefins, alkanols etc. from synthesis gas. Of particular note, U.S. Pat. No. 2,636,046, discloses the synthesis of polyhydric alcohols and their derivatives by reaction between carbon monoxide and hydrogen at elevated pressures (>1500 atm or 22000 psi) and temperatures of >150° C. using certain cobalt-containing catalysts. The reaction of carbon monoxide and hydrogen in the presence of a ruthenium catalyst and a pyridine base ligand to form ethylene glycol is set out in U.S. Pat. No. 4,170,605. Also recently, in Belgium Pat. No. 793,086 and U.S. Pat. No. 3,940,432 there is described the co-synthesis of methanol and ethylene glycol from mixtures of carbon monoxide and hydrogen using a rhodium complex catalyst. Typically, CO-hydrogenation is effected at 8000 psi of 1:1 $H_2/CO$ synthesis gas, at 220° C., using tetraglyme as the solvent, and dicarbonylacetylacetonatorhodium(I) in combination with promoters such as pyridine and its derivatives as the catalyst precursor. (For summary of the work, see: R. L. Pruett, Annals New York Academy of Sciences, Vol. 295 p. 239 (1977)). While other metals of Group VIII of the Periodic Table have been tested for activity under similar conditions, including cobalt, ruthenium, copper, manganese, iridium and platinum, only cobalt was found to have slight activity. The use of ruthenium compounds in particular failed to produce polyfunctional products such as ethylene glycol. This is illustrated in U.S. Pat. No. 3,833,634 for solutions of triruthenium dodecacarbonyl.

SUMMARY OF THE INVENTION

In this invention ethylene glycol is prepared by reaction of carbon monoxide and hydrogen in the presence of a ruthenium compound, a promoter and a solvent at an elevated temperature and pressure. In another embodiment, this invention relates to the production of ethylene glycol ethers by reaction of carbon monoxide and hydrogen in the presence of a ruthenium compound, a promoter and a mineral acid.

Surprisingly, it has been found that when the reaction of carbon monoxide and hydrogen is conducted in the presence of a ruthenium compound and a promoter, such as pyrocatechol, polyfunctional products are formed.

DETAILED DESCRIPTION OF THE INVENTION

This invention relates to a process for preparing ethylene glycol which comprises reacting a mixture of hydrogen and carbon monoxide in the presence of a ruthenium compound and a promoter at a temperature of about, 125° to about 300° C. and at a pressure of about 1000 psi to about 10,000 psi and wherein the reaction is conducted in the presence of a solvent of the formula:

$$R(OCH_2CH_2)_nOR'$$

wherein R is alkyl having from 1 to 4 inclusive carbon atoms and R' is selected from the group consisting of hydrogen and alkyl having from 1 to 4 inclusive carbon atoms, and n is an integer of from 2 to 4 inclusive.

In another aspect this invention relates to a process for preparing ethylene glycol ethers which comprises reacting a mixture of carbon monoxide and hydrogen in the presence of a ruthenium compound catalyst and a promoter at a temperature of about 125° to about 300° C. and at a pressure of about 1000 to about 10,000 psi and wherein the reaction is conducted in the presence of a solvent and a mineral acid.

The ruthenium compound catalyst employed in the process of this invention may be chosen from a wide variety of organic inorganic compounds, complexes, etc., as will be shown and illustrated below. It is only necessary that the ruthenium compound utilized contain ruthenium in any of its normal oxidation states. The actual catalytically active species is believed to comprise ruthenium in complex combination with carbon monoxide and hydrogen.

The ruthenium may be added to the reaction mixture in an oxide form, as in the case of, for example, ruthenium(IV) oxide, hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, anhydrous ruthenium(III) chloride and ruthenium nitrate, or as the salt of a suitable organic carboxylic acid (see below), for example, ruthenium(III) acetate, ruthenium(III) propionate, ruthenium butyrate, ruthenium(III) trifluoroacetate, ruthenium octanoate, ruthenium napththenate, ruthenium valerate and ruthenium(III) acetylacetonate. The ruthenium may also be added to the reaction zone as a carbonyl or hydrocarbonyl derivative. Here, suitable examples include triruthenium dodecacarbonyl, hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

In a preferred embodiment of the invention ruthenium is added to the reaction zone as one or more oxide, salt or carbonyl derivative species in combination with one or more Group VB, as set out on page 125 of Mellor's, Modern Inorganic Chemistry, 1967, tertiary donor ligands. The key elements of the Group VB ligands include nitrogen, phosphorous, arsenic and antimony. These elements, in their trivalent oxidation states, particularly tertiary phosphorous and nitrogen, may be bonded to one or more alkyl, cycloalkyl, aryl, substituted aryl, aryloxide, alkoxide and mixed alkaryl radicals, each containing from 1 to 12 carbon atoms, or they may be part of a heterocyclic ring system, or be mixtures thereof. Illustrative examples of suitable ligands that may be used in this invention include: triphenylphosphine, tri-n-butylphosphine, triphenylphosphite, triethylphosphite, trimethylphosphite, trimethylphosphine, tri-p-methoxyphenylphosphine, triethylphosphine, trimethylarsine, triphenylarsine, tri-p-tolylphosphine, tricyclohexylphosphine, dimethylphenylphosphine, trioctylphosphine, tri-o-tolyphosphine, 1,2-bis(diphenylphosphino)ethane, triphenylstibine, trimethylamine, triethylamine, tripropylamine, tri-n-octylamine, pryidine, 2,2'-dipyridyl, 1,10-phenanthroline, quinoline, N,N'dimethylpiperazine, 1,8-bis(dimethylamino)naphthalene and N,N-dimethylaniline.

One or more of these ruthenium-tertiary Group VB donor ligand combinations may be preformed, prior to addition to the reaction zone, as in the case, for example, of tris(triphenylphosphine)ruthenium(II) chloride and dicarbonylbis(triphenylphosphine)ruthenium(II) chloride or alternatively, said complexes may be formed in situ.

The quantity of ruthenium catalyst employed in the instant invention is not critical and may vary over a wide range. In general, the novel process is desirably conducted in the presence of a catalytically effective quantity of one or more of the active ruthenium species together with the promoter which gives the desired products in reasonable yields. The reaction proceeds when employing as little as about 0.001 weight percent and even lesser amounts of ruthenium, basis the total weight of the reaction mixture. The upper concentration is dictated by a variety of factors including catalyst cost, partial pressures of carbon monoxide and hydrogen, operating temperature, etc. A ruthenium catalyst concentration of from about 0.01 to about 10 weight percent ruthenium, based on the total weight of reaction mixture, is generally desirable in the practice of this invention.

Promoters useful in the process of this invention include polyhydric phenols such as pyrocatechol, resorcinol, quinol, pyrogallol, hydroxyquinol, phloroglucinol, alkylated dihydroxybenzenes such as orcinol, dihydroxynaphthalenes and diphenols such as O,O'-diphenol as well as mixtures of these materials.

The number of gram moles of the promoter employed per gram atom of ruthenium can be varied widely and is generally in the range of about 0.1 to about 100 and preferably from about 1.0 to about 10.

Solvents suitable for use in the process of this invention have the formula:

$$R(OCH_2CH_2)_nOR'$$

wherein R is alkyl having 1 to 4 inclusive carbon atoms and R' is selected from the group consisting of hydrogen and alkyl having from 1 to 4 inclusive carbon atoms as exemplified by diethylene glycol monomethyl ether, diethylene glycol dimethyl ether, diethylene glycol monoethyl ether, diethylene glycol diethyl ether, diethylene glycol monobutyl ether, diethylene glycol dibutyl ether, triethylene glycol dimethyl ether, tetraethylene glycol dimethyl ether, tetraethylene glycol monopropyl ether, etc.

In the embodiment of this invention relating to the process for preparing ethylene glycol ethers by reaction of carbon monoxide and hydrogen conducted in the presence of a ruthenium compound, a promoter, solvent and a mineral acid, the suitable mineral acids include sulfuric acid, hydrochloric acid and phosphoric acid. The number of gram moles of the mineral acid used per gram atom of ruthenium can be varied over a wide range and generally will be in the range of about 1.0 to about 100.

The temperature range which can usefully be employed in this process is a variable dependent upon other experimental factors, including the pressure, and the concentration and choice of particular species of the ruthenium-containing compound and the promoter among other things. The range of operability is from about 125° to about 300° C. when superatmospheric pressures of syngas are employed. A narrower range of about 150° to about 250° C. represents the preferred temperature range.

Superatmospheric pressures of 1000 psi or greater lead to substantial yields of the desired ethylene glycol or glycol ethers by the process of this invention. A preferred operating range is from about 1500 psi to about 7500 psi, although pressures above 7500 psi also provide useful yields of the desired end products. The pressures referred to here represent the total pressure generated by all the reactants, although they are substantially due to the carbon monoxide and hydrogen fractions in these examples.

The relative amounts of carbon monoxide and hydrogen which may be initially present in the syngas mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether.

In all these syntheses in order to achieve a high degree of selectivity the amount of carbon monoxide and hydrogen present in the reaction mixture should be sufficient to at least satisfy the stoichiometry involved in forming the desired ethylene glycol or corresponding ethers. Excess carbon monoxide and/or hydrogen over the stoichiometric amounts may be present, if desired.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ethylene glycol or glycol ether products, and said material may be recovered by methods well known in the art, such as distillation, fractionation, extraction and the like. A fraction rich in the ruthenium catalyst and promoter may then be recycled to the reaction zone, if desired, and additional products generated.

The products have been identified in this work by one or more of the following analytical procedures, viz, gas-liquid phase chromatography (GLC), Fourier Transform infrared spectrometry (FTIR), nuclear magnetic resonance (nmr) and elemental analyses, or a combination of these techniques. Analyses have, for the most part, been by parts in weight; all temperatures are in degrees centigrade and all pressures in pounds per square inch gauge (psi).

The following examples which illustrate various embodiments of the invention are to be considered not limitative.

EXAMPLE I

To a degassed sample of tetraglyme, i.e., $CH_3(OCH_2CH_2)_4OCH_3$(25 g) contained in a glass-lined reactor equipped for pressurizing, heating and means of addition was added, under a nitrogen environment, tris(triphenylphosphine)ruthenium(II) chloride (0.96 g, 1.0 mmole) and pyrocatechol (0.88 g, 8 mmoles). The reactor was sealed, flushed with a mixture of carbon monoxide and hydrogen (1:1 molar) and pressured to 2000 psi with the same gaseous mixture. The reactor was heated to 220° with rocking, and the pressure raised to 6300 psi through the addition of the gaseous mixture (1:1 molar $CO/H_2$) from a large surge tank after which the reactor was held at 220° C. for 18 hours.

Upon cooling and depressuring of the reactor, 28.1 g of clear, deep red, liquid product was recovered. There was no solid fraction. Analysis of the liquid product by GLC and FTIR techniques on a solvent free basis gave the following results:

| COMPOUND | SELECTIVITY, WT. % |
|---|---|
| Ethylene Glycol | 11 |
| Methanol | 42 |
| Ethanol | 8 |
| Methyl Formate | 5 |
| Water | 11 |

The remainder of the sample was primarily pyrocatechol together with unidentified materials.

Samples of off-gas typically showed the following composition:
43% hydrogen
53% carbon monoxide
2.3% carbon dioxide

EXAMPLE II

The procedure of Example I was followed with the exception that 0.244 g of dicarbonylbis(triphenylphosphine)-ruthenium(II) chloride was used as the ruthenium source.

The liquid product, recovered from the reactor after the 18 hour reaction period, when analyzed by GLC on a solvent free basis gave the following results:

| COMPOUND | SELECTIVITY, WT. % |
|---|---|
| Ethylene Glycol | 5 |
| Methanol | 14 |
| Ethanol | 3 |
| Water | 8 |
| Methyl Formate | 5 |

Samples of off-gas from this run typically showed the following composition:
43% hydrogen
55% carbon monoxide
1.2% carbon dioxide

EXAMPLE III

The procedure of Example I was followed with the exception that ruthenium(III) acetylacetonate (0.398 g, 1.0 mmole) provided the source of ruthenium.

The products of the reaction were essentially the same as in Example I and analysis of the liquid product showed the following weight percent selectivities:

| COMPOUND | SELECTIVITY WT. % |
|---|---|
| Ethylene glycol | 3 |
| Methanol | 24 |
| Methyl Formate | 3 |

-continued

| COMPOUND | SELECTIVITY WT. % |
|---|---|
| Water | 13 |

The remainder of the sample was primarily pyrocatechol plus unidentified materials.

Samples of off-gas from this run typically showed the following composition:
44% hydrogen
55% carbon monoxide
1.5% carbon dioxide

EXAMPLE IV

The procedure of Example I was followed with the exception that ruthenium dodecacarbonyl (0.213 g, 1.0 mmole Ru) was the source of ruthenium and 1.67 g of sulphuric acid (95%) was added to the tetraglyme solvent. The reaction was allowed to proceed for 6 hours at 220° C.

The deep red liquid product (27.7 g) recovered again showed no evidence of solid precipitate. An analysis by GLC and FTIR gave the following selectivities on a solvent free basis:

| COMPOUND | SELECTIVITY, WT. % |
|---|---|
| Ethylene Glycol monomethyl ether | 12 |
| Ethylene glycol dimethyl ether | 12 |
| Methanol | 9 |
| Water | 39 |

The remainder of the sample was primarily pyrocatechol, 1,4-dioxane and unidentified materials.

What is claimed is:

1. A process for the preparation of ethylene glycol which comprises reacting carbon monoxide and hydrogen in the presence of a ruthenium compound and one or more polyhydric phenols at a temperature of about 125° to about 300° C. and at a pressure of about 1000 psi to about 10,000 psi and wherein the said reaction is conducted in the presence of a solvent having the formula:

$$R(OCH_2CH_2)_nOR'$$

wherein R is alkyl having 1 to 4 inclusive carbon atoms and R' is selected from the group consisting of hydrogen and alkyl having 1 to 4 inclusive carbon atoms, and n is an integer of from 2 to 4 inclusive.

2. The process of claim 1 wherein the reaction is conducted in the presence of polyhydric phenol selected from the group consisting of pyrocatechol, resorcinol, quinol, pyrogallol, hydroxyquinol, phloroglucinol, orcinol, dihydroxynaphthalene and 0,0'-diphenol.

3. The process of claim 1 wherein the said reaction is conducted at a temperature of about 150° to about 250° C.

4. The process of claim 1 wherein the said reaction is conducted at a pressure of about 1500 psi to about 7500 psi.

5. The process of claim 1 wherein the said ruthenium compound is selected from the group consisting of tris(triphenylphosphine)ruthenium(II) chloride, dicarbonylbis(triphenylphosphine)ruthenium(II) chloride, ruthenium(III) acetylacetonate and ruthenium dodecacarbonyl.

6. The process of claim 1 wherein the said ruthenium compound is tris(triphenylphosphine)ruthenium(II) chloride.

7. The process of claim 1 wherein the said ruthenium compound is dicarbonylbis(triphenylphosphine)ruthenium(II) chloride.

8. The process of claim 1 wherein the said ruthenium compound is ruthenium(III) acetylacetonate.

9. The process of claim 1 wherein the said ruthenium compound is ruthenium dodecacarbonyl.

10. The process of claim 1 wherein the said solvent is $CH_3(OCH_2CH_2)_2OCH_3$.

11. The process of claim 1 wherein the said solvent is $CH_3(OCH_2CH_2)_4OCH_3$.

12. The process of claim 1 wherein the said promoter is pyrocatechol.

13. The process of claim 1 wherein the said ruthenium compound is tris(triphenylphosphine)ruthenium(II) chloride, the said promoter is pyrocatechol and the said solvent is $CH_3(OCH_2CH_2)_4OCH_3$.

14. The process of claim 1 wherein the said ruthenium compound is dicarbonylbis(triphenylphosphine)ruthenium(II) chloride, the said promoter is pyrocatechol and the said solvent is $CH_3(OCH_2CH_2)_4OCH_3$.

15. The process of claim 1 wherein the said ruthenium compound is ruthenium(III) acetylacetonate, the said promoter is pyrocatechol and the said solvent is $CH_3(OCH_2CH_2)_4OCH_3$.

* * * * *